Figure 1:
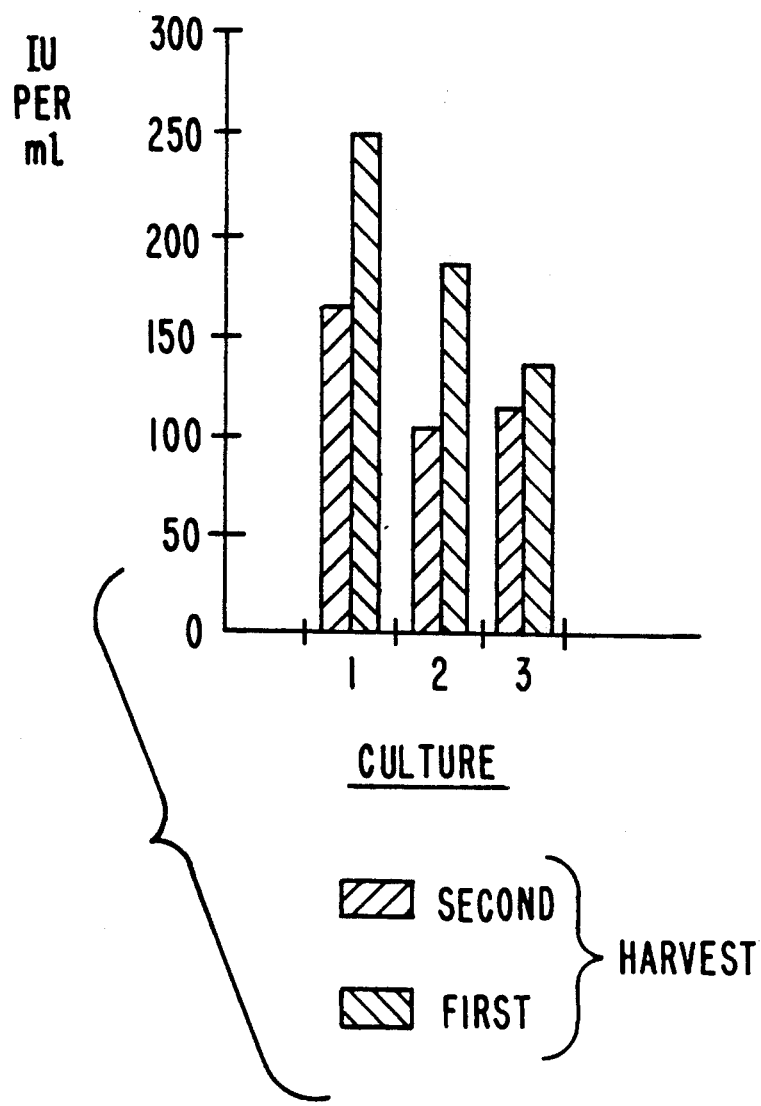

United States Patent [19]

Kearns et al.

[11] Patent Number: 5,002,877

[45] Date of Patent: Mar. 26, 1991

[54] PRODUCTION OF PLASMINOGEN ACTIVATOR FROM CELLS TO WHICH LECTIN IS ADDED TO THE CULTURE MEDIUM

[75] Inventors: Michael J. Kearns; Ian J. McEntee; John R. North, all of Salisbury, United Kingdom

[73] Assignees: Porton Products Ltd; Public Health Lab. Service BD, both of London, United Kingdom

[21] Appl. No.: 465,111

[22] PCT Filed: Sep. 16, 1988

[86] PCT No.: PCT/GB88/00758

§ 371 Date: Feb. 22, 1990

§ 102(e) Date: Feb. 22, 1990

[87] PCT Pub. No.: WO89/02917

PCT Pub. Date: Apr. 6, 1989

[30] Foreign Application Priority Data

Oct. 1, 1987 [GB] United Kingdom ............... 8723082

[51] Int. Cl.$^5$ ............................................. C12P 21/04
[52] U.S. Cl. ................................. 435/70.3; 435/212; 435/70.1; 435/240.1
[58] Field of Search .................. 435/212, 240.1, 70.1, 435/70.3

[56] References Cited

U.S. PATENT DOCUMENTS 4,780,412 10/1988 Atkinson .............................. 435/68
4,889,808 12/1989 Rappaport ...................... 435/240.1

FOREIGN PATENT DOCUMENTS 133070 2/1985 European Pat. Off. .
158958 10/1985 European Pat. Off. .
219270 4/1987 European Pat. Off. .

OTHER PUBLICATIONS

Derwent's Abstract No. 88-216871/31, JP 63152977.
Chemical Abstracts, vol. 102, No. 7, Feb. 18, 1985, (Columbus, Ohio, U.S.), Schuyler, M. et al., p. 406, abstract 59984b.
Chemical Abstracts, vol. 92, No. 7, Feb. 18, 1980, (Columbus, Ohio, U.S.), Mochan, E., p. 148, abstract 52788g.
Chemical Abstracts, vol. 105, No. 13, Sep. 29, 1986, (Columbus, Ohio, U.S.), Katayama, I. et al., pp. 536–537, abstract 113390g.
Brouty-Boye, G. et al., *Bio/Technology*, Dec., p. 1058, 1984.

*Primary Examiner*—Richard A. Schwartz
*Assistant Examiner*—Marianne Porta
*Attorney, Agent, or Firm*—Eugene M. Bond

[57] ABSTRACT

Increased yields of enzymes, particularly tissue plasminogen activator (tPA), are produced from cells, particularly CNCM I-222 cells, by a process using less concentrated lectin, particularly concanavalin A, in culture medium added to replace initial growth medium than has been used hitherto. After first harvesting of enzyme in supernatants, the culture can be reactivated by the addition of fresh culture medium containing an even lower lectin concentration, and a further harvest of enzyme obtained. The two harvests of enzyme together can give a greater overall yield than a single harvest after a single induction step employing the conventionally used higher lectin concentrations. Enzyme yield can be further increased by repeating the last incubation step once or twice to obtain one or two further harvests.

1 Claim, 1 Drawing Sheet

PRODUCTION OF PLASMINOGEN ACTIVATOR FROM CELLS TO WHICH LECTIN IS ADDED TO THE CULTURE MEDIUM

FIELD OF THE INVENTION

This invention concerns the production of enzymes from cells, particularly from cell lines such as CNCM I-222 which produces tissue plasminogen activator (tPA).

BACKGROUND OF THE INVENTION

In a paper by J. B. Griffiths and A. Electricwala entitled "Amplification of Tissue Phasminogen Activator Expression from Epithelial Lines" given at the 7th General Meeting of ESACTR on Advances in Aninmal Cell Technology: Cell Engineering Evaluation and Exploitation, at Baden, Australia, 1985 and published in Develop. biol. Standard., Volume 66 pages 417–422 (S. Karger, Basel 1987), reference is made to a process for achieving expression of tPA from established epithelial cell lines, one derived from human breast tissue (BEB) and another from guinea pig ear keratocytes (GPK). The GPK cell line has been deposited in the Collection Nationale de Cultures de Microorganismes (CNCM) at the Institute Pasteur in Paris, France under accession number CNCM I-222.

The enzyme was found to be mainly expressed during the cell growth phase rather than from stationary culture cells, and production involved a two-step operation with initial growth to about 70% confluency in the presence of serum followed by a change to serum-free conditions for the final period of growth, after which the enzyme was harvested.

The paper discusses various approaches to increase the enzyme yield. The addition of mitogenic lectins was reported to increase the enzyme yield 15-20 fold.

In a typical enzyme production process based on this approach, cells are inoculated into roller bottles and incubated at 36.5° C. for 72 hours in culture medium containing animal serum, resulting in growth to about 70% confluency. At the end of the 72 hours the growth medium is poured off, the cell washed twice and the medium replaced with half the original volume of culture medium containing no serum but with 50 microgarms/ml of a lectin, the most effective of which was found to be concanavalin A. Experiments showed this to be the optimum concentration of concanavalin A. The cultures are then incubated in the presence of lectin for a further 48 hours at 36.5° C. after which supernatants (containing enzyme) are harvested and the cultures discarded.

SUMMARY OF THE INVENTION

According to the present invention it has been found that by employing less concentrated lectin in the culture medium added to replace the initial growth medium than is used in the prior art process, the culture can be reactivated after the first harvesting of enzyme by the addition of fresh culture medium containing an even lower lestin concentration, and after incubation for a similar period of time a further harvest of supernatants containing the desired enzyme can be harvested. The two harvests of enzyme together can give a greater overall yield than a single harvest after a single induction step employing the previously used higher lectin concentration.

Hence, according to the present invention there is provided a process for producing an enzyme from cells, comprising incubating cells in culture medium at a suitable temperature and for a suitable time to produce growth of the cells; removing the growth medium; adding a further supply of fresh culture medium containing a lectin at a first concentration substantially less than 50 micrograms/ml but containing no serum; incubating the culture at a suitable temperature and for a suitable time for production of enzyme from the cells; harvesting supernatants including the desired enzyme; adding to the culture after harvesting of the supernatants a further supply of fresh culture medium containing a lectin at a second concentration lower than said first concentration but containing no serum; incubating the culture at a suitable temperature and for a suitable time for production of enzyme from the cells; and harvesting supernatants including the desired enzyme.

It has been found that the enzyme yield can be further increased by repeating the last incubation step once or twice, by the addition of fresh serum-free "induction" medium containing the very low lectin concentration after the second harvesting. In this way a total of up to four harvests can be obtained before the culture is discarded.

The various incubation steps are generally carried out at a temperature of 36.5° C. ($\pm 1°$ C.).

The first incubation is conveniently carried out for sufficient time to produce cell growth to about 70% confluency. This typically takes about 72 hours, although the length of this incubation period is not critical to within an hour or so.

The second incubation, and any subsequent incubations, are preferably carried out for about 48 hours to obtain maximum enzyme yield, but the length of these incubation periods is not critical to within an hour or so.

The lectin preferably comprises concanavalin A as this has been found to give the best enzyme yields, but other lectins such as wheat germ agglutinin and other mitrogenic lectins can also be used.

For optimum results the first concentration of lectin is preferably 20 micrograms/ml, with this value being reduced to 10 micrograms/ml where the cells are grown on the surface of micro-carrier beds of suitable material, e.g. dextran or gelain, and the second concentration of lectin is preferably 5 micrograms/ml. Other concentrations can be used, but give less good results.

The culture medium may comprise any suitable medium, such as the media that are conventionally used for this purpose. Good results have been obtained with Eagle's minimum essential medium (MEM) supplemented with serum, e.g. foetal calf serum. Other suitable cell culture medium formulations include, e.g., Ex-cell 300 medium (JR Scientific, Davis, Calif.) without serum.

The invention is applicable to the production of a range of different enzymes from a range of different cell types, but finds particular application in the production of tPA from the BEB or GPK cells, the latter conveniently being obtained from the CNCM I-222 cell line.

Hence in a preferred aspect of the present invention provides a process for the production of tPA from CNCM I-222 cells, comprising incubating cells in culture medium at about 36.5° C. for about 72 hours to produce a growth of the cells; removing the growth medium; adding a further supply of fresh culture medium containing concanavalin A at a concentration not exceeding 20 micrograms/ml but containing no serum;

incubating the culture at about 36.5° C. for about 48 hours, resulting in production of tPA from the cells; harvesting supernatants including the tPA; adding to the culture after harvesting of the supernatants a further supply of fresh culture medium containing concanavalin A at a second concentration of about 5 micrograms/ml but containing no serum; incubating the culture at about 36.5° C. for about 48 hours, resulting in production of tPA from the cells; and harvesting supernatants including the tPA.

The invention also includes within its scope enzyme, particularly tPA, produced by the process of the invention.

The invention will be further described, by way of illustration, in the following example and with reference to the accompanying drawing the single FIGURE of which is a graph illustrating yields of tPA in a preferred process embodying the invention.

EXAMPLE

Cells from the GPK cell line CNCN I-222 were inoculated into a roller bottles and incubated at 36.5° C. ($\pm 1°$ C.) for 72 hours in growth medium comprising Eagle's minimum essential medium (MEM) supplemented with 10% foetal calf serum (FCS) from Imperial Laboratories, Salisbury, UK, resulting in growth to about 70% confluency.

After incubation the growth medium was poured off and the cells washed twice with phosphate-buffered saline. About half the original volume of Eagle's MEM was then added to the cells, this "induction" medium containing no serum but containing 20 micrograms/ml of the lectin concanavalin A. The cultures were incubated for a further 48 hours at 36.5° C. ($\pm 1°$ C.), resulting in expression of tPA. Supernatants containing tPA were then harvested.

Fresh Eagle's MEM containing no serum but containing 5 micrograms/ml of concanavalin A was then added to the cells, and the cultures incubated for a further 48 hours at 36.5° C. ($\pm 1°$ C.), resulting in further expression of tPA. Supernatants containing tPA were then harvested.

The graph of FIG. 1 illustrates in columns 1 to 2 typical yields of enzyme in the first and second harvests in 3 separate experiments.

The two harvests of the enzyme together can give a greater overall yield than is obtained in the prior art process, including a single harvest after a single incubation step at higher lectin concentration.

The yield of tPA can be further increased by repeating the last incubation step once or twice, i.e. for 48 hours in the presence of induction medium containing no serum but containing 5 micrograms/ml concanavalin A, followed by further harvesting of supernatants containing tPA. In this way a further 1 or 2 harvests may be produced, resulting in a maximum of 4 possible harvests, after which the cultures are discarded.

When carrying out the above procedure with cultures of cells grown on the surface of micro-carrier beads composed of a suitable material, e.g. dextran or gelain, it is recommended that the initial concentration of the lectin be reduced to 10 micrograms/ml from 20 micrograms/ml, with other conditions remaining as described above.

We claim:

1. A process for the production of tPA from CNCM I-222 cells, comprising incubating cells in culture medium at about 36.5° C. for about 72 hours to produce growth of the cells; removing the growth medium; adding a further supply of fresh culture medium containing concanavalin A at a concentration about but no exceeding 20 micrograms/ml but containing no serum; incubating the culture at about 36.5° C. for about 48 hours, resulting in production of tPA from the cells; harvesting supernatants including the tPa; adding to the culture after harvesting of the supernatants a further supply of fresh culture medium containing concanavalin A at a concentration of about 5 micrograms/ml but containing no serum; incubating the culture at about 36.5° C. for about 48 hours, resulting in production of tPA from the cells; and harvesting supernatants including the tPA.

* * * * *